United States Patent [19]
Carroll et al.

[11] Patent Number: 6,058,784
[45] Date of Patent: May 9, 2000

[54] MATERIAL TESTING APPARATUS HAVING SEPARATED LOAD GENERATING MECHANISMS

[75] Inventors: Paul J. Carroll, Maple Grove; Mark J. Fuller, Eden Prairie; Robert J. Orange, Bloomington, all of Minn.

[73] Assignee: MTS Systems Corporation, Eden Prairie, Minn.

[21] Appl. No.: 09/017,837

[22] Filed: Feb. 3, 1998

[51] Int. Cl.⁷ ........................................... G01N 3/08
[52] U.S. Cl. ............................... 73/856; 73/831
[58] Field of Search ..................... 73/794, 796, 831, 73/856, 857, 858, 859, 860

[56] References Cited

U.S. PATENT DOCUMENTS

| | | | |
|---|---|---|---|
| 4,011,749 | 3/1977 | Cappel | 73/71.6 |
| 4,145,956 | 3/1979 | Rumrill, Jr. et al. | 91/380 |
| 4,293,002 | 10/1981 | Moriyama et al. | 137/625.64 |
| 4,403,511 | 9/1983 | Shibano et al. | 73/665 |
| 4,741,364 | 5/1988 | Stoss et al. | 137/625.64 |
| 4,748,851 | 6/1988 | Yoneda | 73/668 |
| 4,856,335 | 8/1989 | Tornberg | 73/597 |
| 4,869,112 | 9/1989 | Gram et al. | 73/856 |
| 4,996,881 | 3/1991 | Tauscher et al. | 73/665 |
| 5,291,787 | 3/1994 | Laforest et al. | 73/663 |
| 5,343,752 | 9/1994 | Woyski et al. | 73/665 |
| 5,425,276 | 6/1995 | Gram et al. | 73/816 |
| 5,431,060 | 7/1995 | Lauren | 73/831 |
| 5,528,942 | 6/1996 | Baratta | 73/856 |
| 5,544,528 | 8/1996 | Woyski et al. | 73/665 |
| 5,581,040 | 12/1996 | Lin | 73/857 |

OTHER PUBLICATIONS

Schenck Brochure (P 2803/2 e): "The VHF 7 Hydropuls®—High–Freqency Materials Testing Machine", Schenck Pegasus (no date).

Application Notes: Model 833 Triaxial Test System for Dynamic Characterization and Fatigue Testing of Elastomers, MTS Systems Corporation, Eden Prairie, MN, 1995.

John M. Davis, "Fitting multi–axis vibration testing into a small laboratory", Test Engineering & Management, Aug./Sep. 1995, pp. 22–23.

*Primary Examiner*—Max Noori
*Attorney, Agent, or Firm*—Westman, Champlin & Kelly, P.A.; S. Koehler

[57] ABSTRACT

A material testing apparatus for applying selected force and moment loads to a test specimen includes a base assembly coupleable to the test specimen. The base assembly includes a support member and a first load generating mechanism adapted to apply a first load to the test specimen. A reaction structure reacts the first load applied to the test specimen. The reaction structure includes a reaction support joined to the support member. A moveable head is coupleable to the test specimen and is moveable relative to the reaction support. A second load generating mechanism is coupled to the moveable head and the reaction support. The second load generating mechanism is adapted to apply selected loads to the test specimen in at least two degrees of freedom.

22 Claims, 4 Drawing Sheets

MATERIAL TESTING APPARATUS HAVING SEPARATED LOAD GENERATING MECHANISMS

BACKGROUND OF THE INVENTION

The present invention relates to a material testing apparatus or system that applies mechanical loads (i.e. forces and/or moments) to a test specimen. More particularly, the present invention relates to a material testing apparatus that applies multiple loads simultaneously.

The physical testing of materials by taking a test specimen and applying tension and/or compressive force loads using an actuator is well known. Commonly, a single actuator is used which, if properly controlled, can apply a single time varying uniaxial force. However, force loading upon a specimen is rarely from a single source at a single frequency. Typically, there exists multiple load sources, each of which apply time varying loads of different frequencies. Accordingly, testing machines have been developed to apply multiple uniaxial force loads simultaneously. One such testing machine is disclosed in U.S. Pat. No. 5,425,276.

Besides uniaxial testing of materials or test specimens, there is also a great need to apply simultaneous multiple mechanical loads, forces and/or moments, in a plurality of degrees of freedom. In this manner, the testing machine can more accurately simulate real life forces and moments applied to a test specimen. For instance, in order to properly perform a dynamic characterization of an engine mount for a vehicle, it is necessary to replicate or simulate as accurately as possible all forces and moments applied to the engine mount when it is mounted in a vehicle. This includes simulating the static force on the engine mount from the weight of the engine, simulating low frequency forces and moments (approximately in the range from 0 to 100 Hz) applied to the engine mount as the vehicle is driven, and simulating high frequency forces and moments (approximately in the range from 100 to 700 Hz) applied to the engine mount, for example, originating from moving components of the engine.

Testing machines have been developed to apply multiple force loads simultaneously along three orthogonal axes. The Model 833 Triaxial Test System sold by MTS Systems Corporation of Eden Prairie, Minnesota, includes flexure coupled actuators that apply force loads along three orthogonal axes to a test specimen. However, the test system cannot apply moments to the test specimen nor can the system apply high frequency loads.

Accordingly, there is a need for an improved testing apparatus that can apply simultaneous loads to a test specimen that includes moments. There is also a need for a testing apparatus that can apply high frequency mechanical loads with respect to a plurality of degrees of freedom.

SUMMARY OF THE INVENTION

A first aspect of the present invention is a material testing apparatus for applying selected force and moment loads to a test specimen. The material testing apparatus includes a base assembly coupleable to the test specimen. The base assembly includes a support member and a first load generating mechanism adapted to apply a first load to the test specimen. A reaction structure reacts the first load applied to the test specimen. The reaction structure includes a reaction support joined to the support member. A moveable head is coupleable to the test specimen and is moveable relative to the reaction support. A second load generating mechanism is coupled to the moveable head and the reaction support. The second load generating mechanism is adapted to apply selected loads to the test specimen in at least two degrees of freedom.

Another aspect of the present invention is a material testing apparatus for applying selected force and moment loads to a test specimen. The material testing apparatus includes a base assembly coupleable to the test specimen. The base assembly includes a support member and a first load generating mechanism adapted to apply a first load to the test specimen. The reaction structure reacts the first load applied to the test specimen. The reaction structure includes a reaction support joined to the support member. A moveable head is coupleable to the test specimen and is moveable relative to the reaction support. A plurality of spaced-apart actuators couple the moveable head to the reaction support. The plurality of spaced-apart actuators are oriented to apply selected loads to the test specimen in at least two degrees of freedom, wherein each actuator applies a linear force along a longitudinal axis of the actuator.

DETAILED DESCRIPTION OF THE PREFERRED EMBODIMENTS

Figure 1:
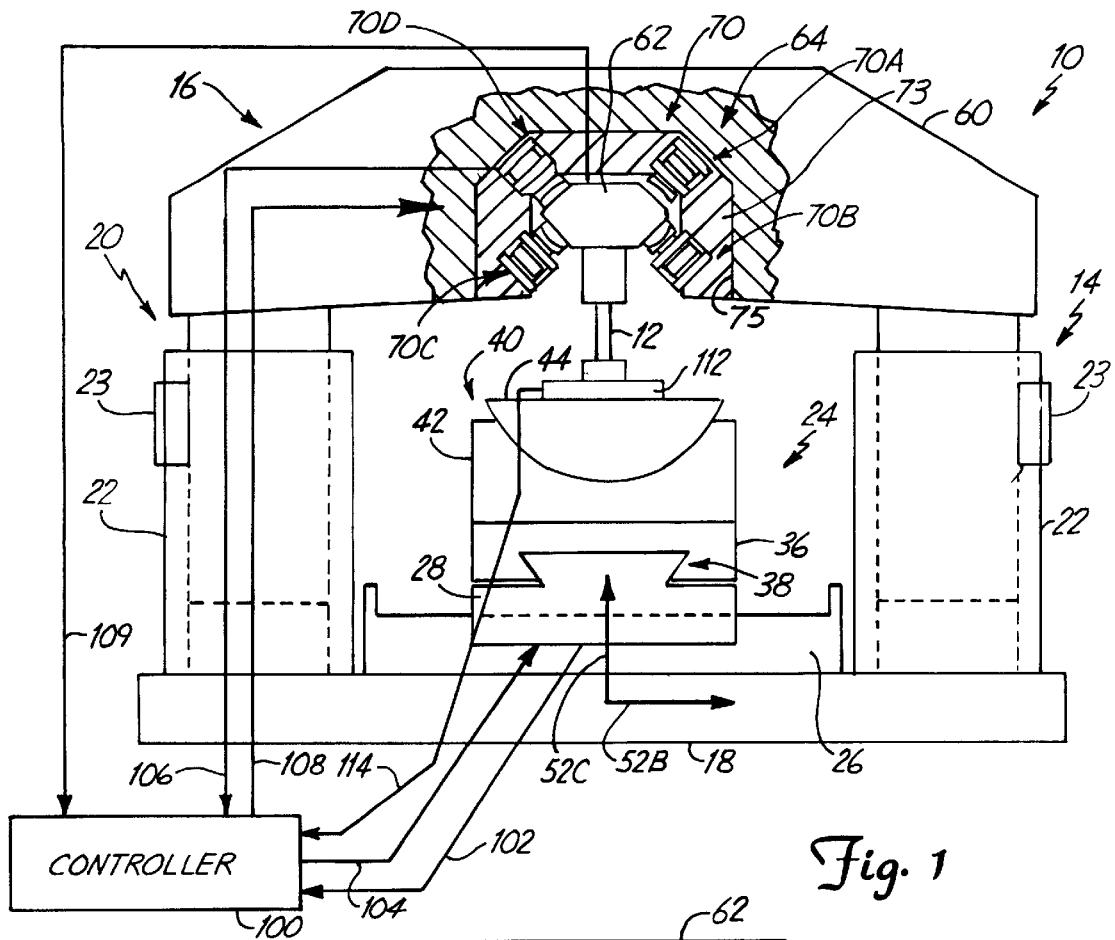
FIG. 1 is a front elevational view of an embodiment of the present invention with a portion removed.
Figure 2:
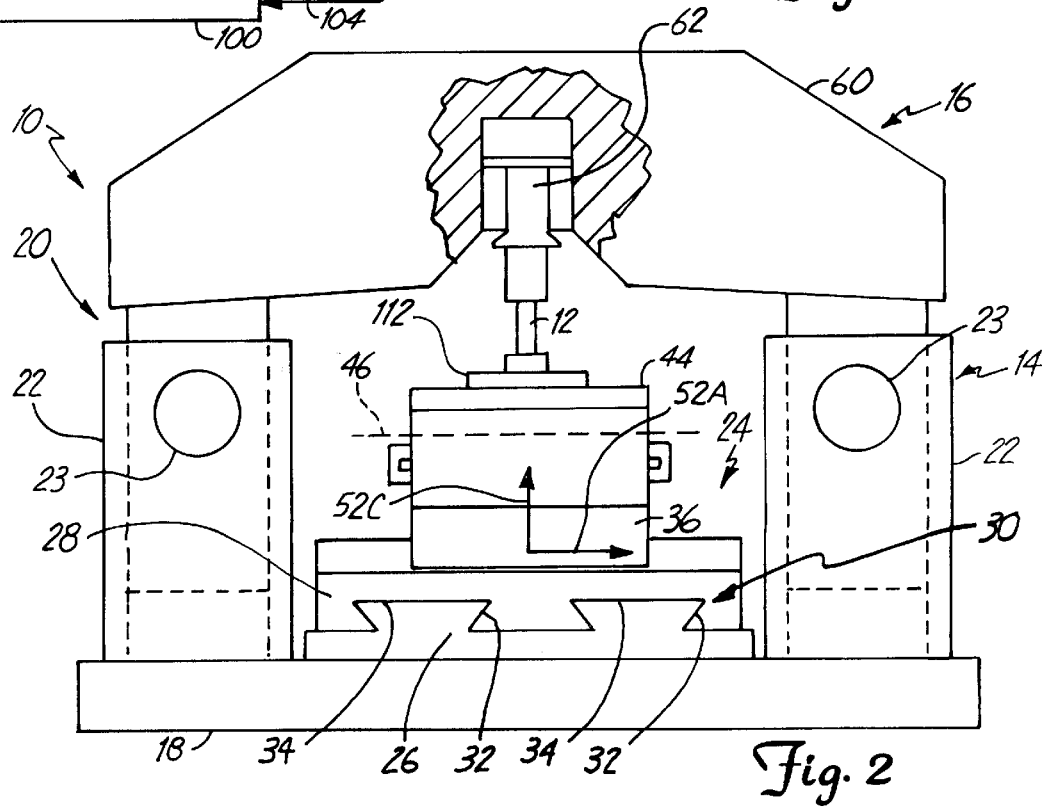
FIG. 2 is a side elevational view of the embodiment of FIG. 1 with a portion removed.

A first embodiment of a material testing apparatus 10 is illustrated in FIGS. 1 and 2. Generally, the material testing apparatus 10 applies selected force and/or moment loads to a test specimen 12. The material testing apparatus 10 includes a base assembly 14 and a reaction structure 16. The base assembly 14 applies a first load (force or moment) to the test specimen 12. The reaction structure 16 reacts the first load applied to the test specimen 12 and provides a second load to the test specimen 12, which is reacted by the base assembly 14. Generally, the base assembly 14 can apply force and moment loads having large displacements and low operating frequencies, while the reaction structure 16 can provide force and moment loads having short displacements and high operating frequencies. In this manner, the material testing apparatus 10 can provide force and moment loads over a wide range of operating requirements in order to simulate real life forces and moments that are applied to the test specimen 12 simultaneously.

In the embodiment illustrated, the base assembly 14 includes a base plate 18 and a vertical support structure 20 illustrated herein as spaced-apart supports 22. The vertical support structure 20 couples the reaction structure 16 to the base plate 18. As appreciated by those skilled in the art, the vertical support structure 20 can be a single column or any one of a number of support columns 22. In the embodiment illustrated, four support columns 22 are provided at corners of the base plate 18. In a preferred embodiment, the support columns 22 are longitudinally adjustable so as to accommodate test specimen 12 of different heights wherein each include an actuator or other suitable displacement device in order to apply tension and/or compressive force loads to the test specimen 12. Clamps 23 can be provided to selectively lock the support columns 22 in place when desired.

The base assembly 14 can also include a biaxial translational table 24. The translational table 24 includes a lower plate 26 secured to the base plate 18. An intermediate plate 28 is slidable on the lower plate 26 wherein the lower plate 26 and the intermediate plate 28 include a suitable slotted connection 30. In the embodiment illustrated, the slotted connection 30 includes rails 32 provided on the lower plate 26 and slots 34 provided in the intermediate plate 28.

An upper plate 36 is coupled to the intermediate plate 28 for slidable displacement thereon in a direction perpendicular to displacement of the intermediate plate 28 on the lower plate 26. The upper plate 36 is coupled to the intermediate plate 28 with a slotted connection 38 similar to the slotted connection 30.

In the embodiment illustrated, the base assembly 14 also includes a rotational displacement assembly 40. The rotational displacement assembly 40 includes a base portion 42 secured to the upper plate 36 and a partial cylindrical member 44. The partial cylindrical member 44 rotates about an axis 46 (FIG. 2). The translational table 24 and the rotational displacement assembly 40 are well known in the art and include suitable actuators or other displacement devices in order to move each of the components described above so as to develop selected forces and moments on the test specimen 12. For purposes of explanation, an orthogonal coordinate system can be defined wherein an X-axis 52A is aligned with movement of the upper plate 36 relative to the intermediate plate 28; a Y-axis 52B is aligned with movement of the intermediate plate 28 relative to the lower plate 26; a Z-axis 52C is aligned with the longitudinal axes of the support columns 22. In the embodiment illustrated, movement of the partial cylindrical member 44 with respect to the base portion 42 corresponds to a moment applied about the X-axis 52A. If desired, the base portion 42 can be rotated 90 degrees so as to develop a moment about the Y-axis 52B. Likewise, if desired, the rotational displacement assembly 40 can include another partial cylindrical member and a base portion similar to that shown in order to allow simultaneous moments about the X-axis 52A and the Y-axis 52B. It should also be noted that a suitable torsional actuator can be provided in the base assembly 14 so as to develop a moment about the Z-axis 52C, if desired.

Figure 3:
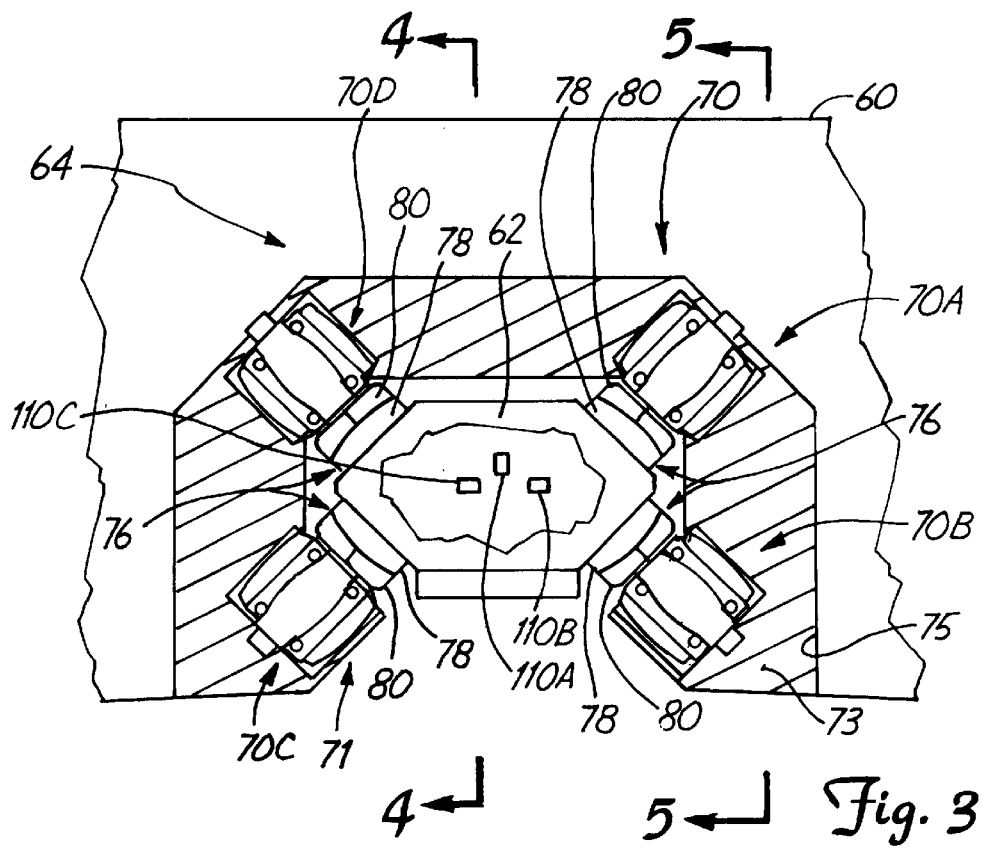
FIG. 3 is an enlarged front elevational view of a load generating mechanism of the embodiment of FIG. 1.
Figure 4:
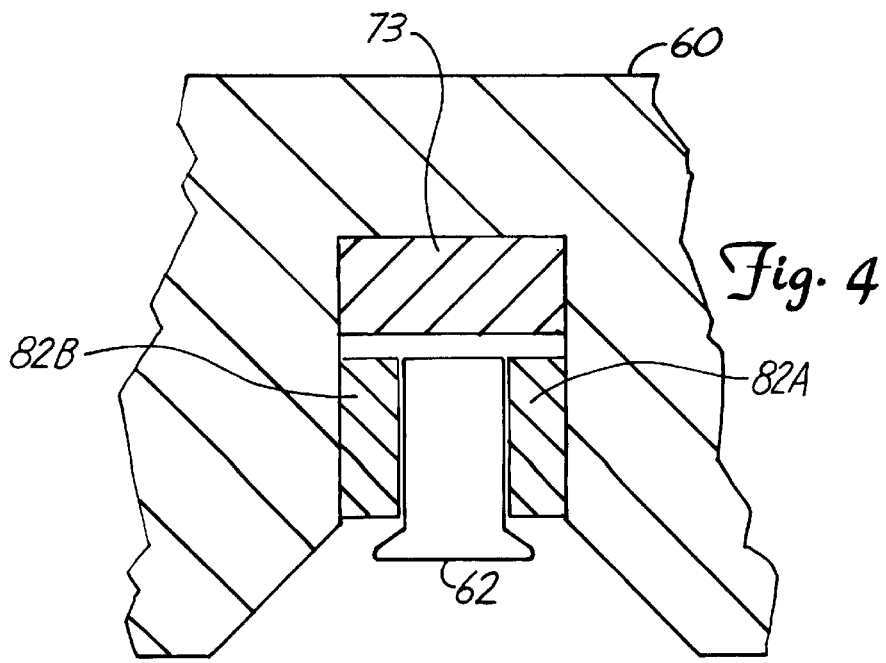
FIG. 4 is a sectional view taken along lines 4—4 in FIG. 3.
Figure 5:
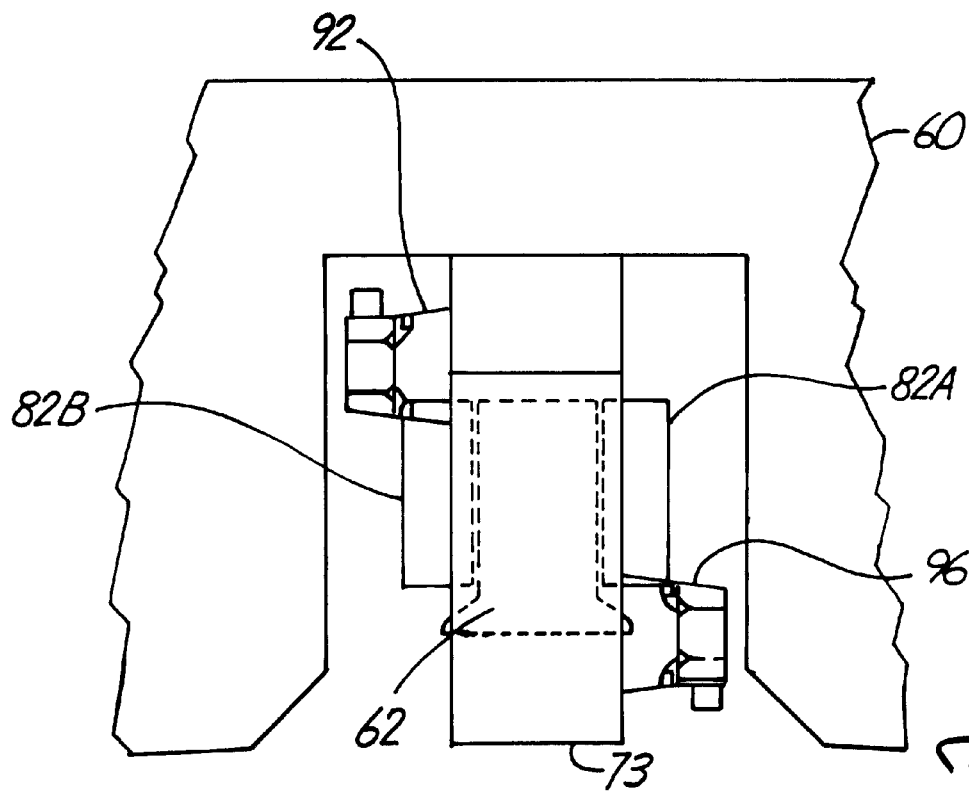
FIG. 5 is a sectional view taken along lines 5—5 in FIG. 3.

Referring also to FIGS. 3–5, the reaction structure 16 includes a reaction support 60 joined to the vertical support structure 20. A moveable head 62 is coupleable to the test specimen 12 and is moveable relative to the reaction support 60. A load generating mechanism or assembly 64 couples the moveable head 62 to the reaction support 60. The load generating mechanism 64 is adapted to apply selected moments or forces over a wide range of operating frequencies, including high frequencies, to the test specimen 12. In the embodiment illustrated in FIGS. 1–5, the load generating mechanism 64 is configured to apply force loads along the Y-axis 52B and the Z-axis 52C as well as a moment about the X-axis 52A.

The load generating mechanism 64 includes a plurality of spaced-apart actuator assemblies 70. In the embodiment illustrated, four spaced-apart actuator assemblies 70A, 70B, 70C and 70D are used. Each actuator assembly 70A–70D engages a planar surface provided on the moveable head 62.

The moveable head 62 is mounted in a recess 71 provided in the reaction support 60. In one embodiment, each of the actuators 70 are mounted in a subframe 73, which in turn is mounted within a recess 75 provided in the reaction support 60. In general, the actuator assemblies 70 are disposed about the recess 71 so as to displace the moveable head 62 in selected degrees of freedom.

To develop the forces and moments described above, the actuator assemblies 70A–70D are grouped in pairs wherein an actuator axis of the actuator assembly 70A is parallel and offset from the actuator axis of the actuator assembly 70C; and the actuator axis of the actuator assembly 70B is parallel and offset from the actuator axis of the actuator assembly 70D. Offsetting the actuator axes allows rotation of the moveable head 62 about the X-axis 52A. In the embodiment illustrated, the actuator axes of the actuator assemblies 70A–70D also intersect obliquely with the axes 52A–52C. For example, in a preferred embodiment, each of the actuator axes of the actuator assemblies 70A–70D intersect with the axes 52A–52C at an angle of approximately 45 degrees.

Each of the actuator assemblies 70A–70D also includes a hydrostatic bearing assembly 76. Each hydrostatic bearing assembly 76 includes a planar hydrostatic bearing allowing planar motion of the moveable head 62 relative to each of the actuator assemblies 70A–70D. The hydrostatic bearing assembly 76 also includes a rotational hydrostatic bearing, such as a cylindrical or spherical hydrostatic bearing, that allows rotational movement of the moveable head 62 relative to each of the actuator assemblies 70A–70D. In the embodiment illustrated, the planar hydrostatic bearing is present between the moveable head 62 and a bearing element 78, which the rotational hydrostatic bearing is present between the bearing element 78 and a cap 80 attached to a piston of the actuator assemblies 70A–70D. Referring to FIG. 4, planar hydrostatic bearings 82A and 82B are further provided on each side of the moveable head 62 so as to restrain movement of the moveable head 62 along the X-axis 52A and about the axes 52B and 52C. If desired, the planar hydrostatic bearings 82A and 82B can be replaced with additional actuators so as to displace the moveable head 62 along the X-axis 52A or about the Z-axis 52C. It should also be understood that the load generating mechanism 64 can include additional actuators and the moveable head 62 can be configured with suitable surfaces so as to displace the moveable head 62 about the Y-axis 52B, if desired.

Figure 6:
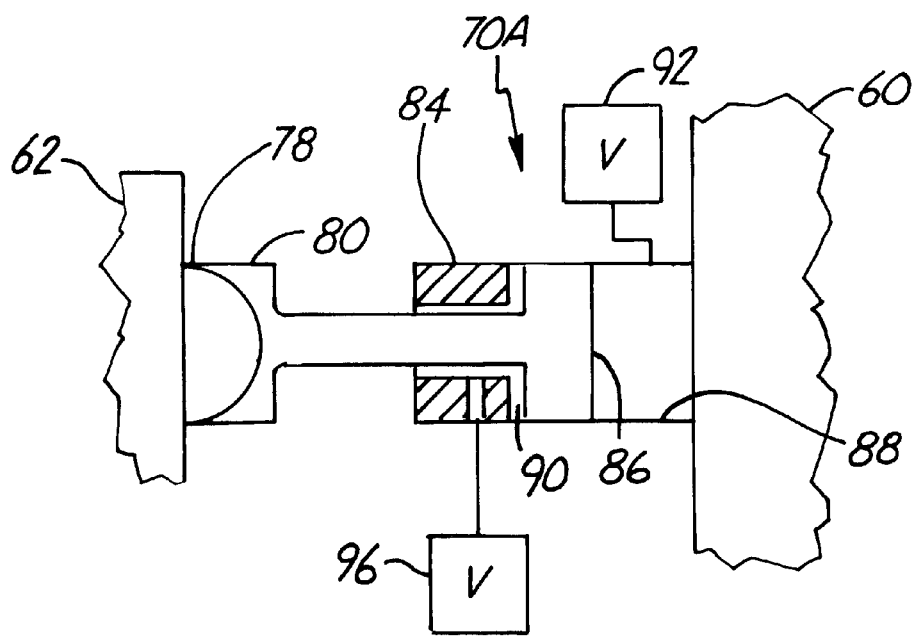
FIG. 6 is a schematic representation of an actuator used in the load generating mechanism of FIG. 3.

A schematic representation of the actuator assembly 70A is illustrated in FIG. 6. In the embodiment illustrated, the actuator assembly 70A is a hydraulic actuator having a housing 84 secured to the reaction support 60. A piston 86 is displaceable in the housing 84 so as to form a first chamber 88 and a second chamber 90. In the embodiment illustrated, the actuator assembly 70A, like the other actuator assemblies 70B–70D, applies only compressive forces between the moveable head 62 and the reaction structure 60. A first valve 92, such as a servovalve, controls fluid flow to the chamber 88, which is maintained at a suitable pressure to react the loads from the base assembly 14. A second valve 96, such as a servovalve, controls fluid flow to the chamber 90 and is varied so as to displace the piston 86 within the housing 84 at desired frequencies, including high frequencies. Preferably, the volume of the chamber 90 is substantially less than the volume of the chamber 88 in order to improve dynamic response.

Referring back to FIG. 1, a controller 100 receives feedback signals and provides suitable control signals to the actuator assemblies 70A–70D and to the displacement devices used in the base assembly 14. Suitable displacement sensors, not shown, are provided on the base assembly 14 to measure relative displacement of each of the moving components of the base assembly 14. A signal line 102 represents feedback position measurements of the base assembly 14, while a signal line 104 represents control signals provided to the displacement devices of the base assembly 14, including control signals for each of the support columns 22. The force applied to the test specimen 12 from the base assembly 14 can be measured as pressure in the chamber 88 of each of the actuator assemblies 70A–70D. A signal line 106 represents a pressure signal from the actuator assembly 70C.

Control signals for the load generating mechanism 64, and in particular for the valves 92 and 96 of the actuator assemblies 70A–70D, are represented by a signal line 108. Feedback can be provided as acceleration of the test specimen 12 on a signal line 109. In the embodiment illustrated, accelerometers 110A, 110B and 110C (FIG. 3) mounted in the moveable head 62 measure acceleration of the moveable head 62 along the axes 52B and 52C as well as rotation about the axis 52A. If desired, feedback can also be provided as a load output as measured by a transducer assembly 112 on a signal line 114. The transducer assembly 112, for example, can be a piezoelectric washer assembly. In one embodiment, control of the actuators 70 will include pressure feedback as represented by the signal line 106.

Figure 7:
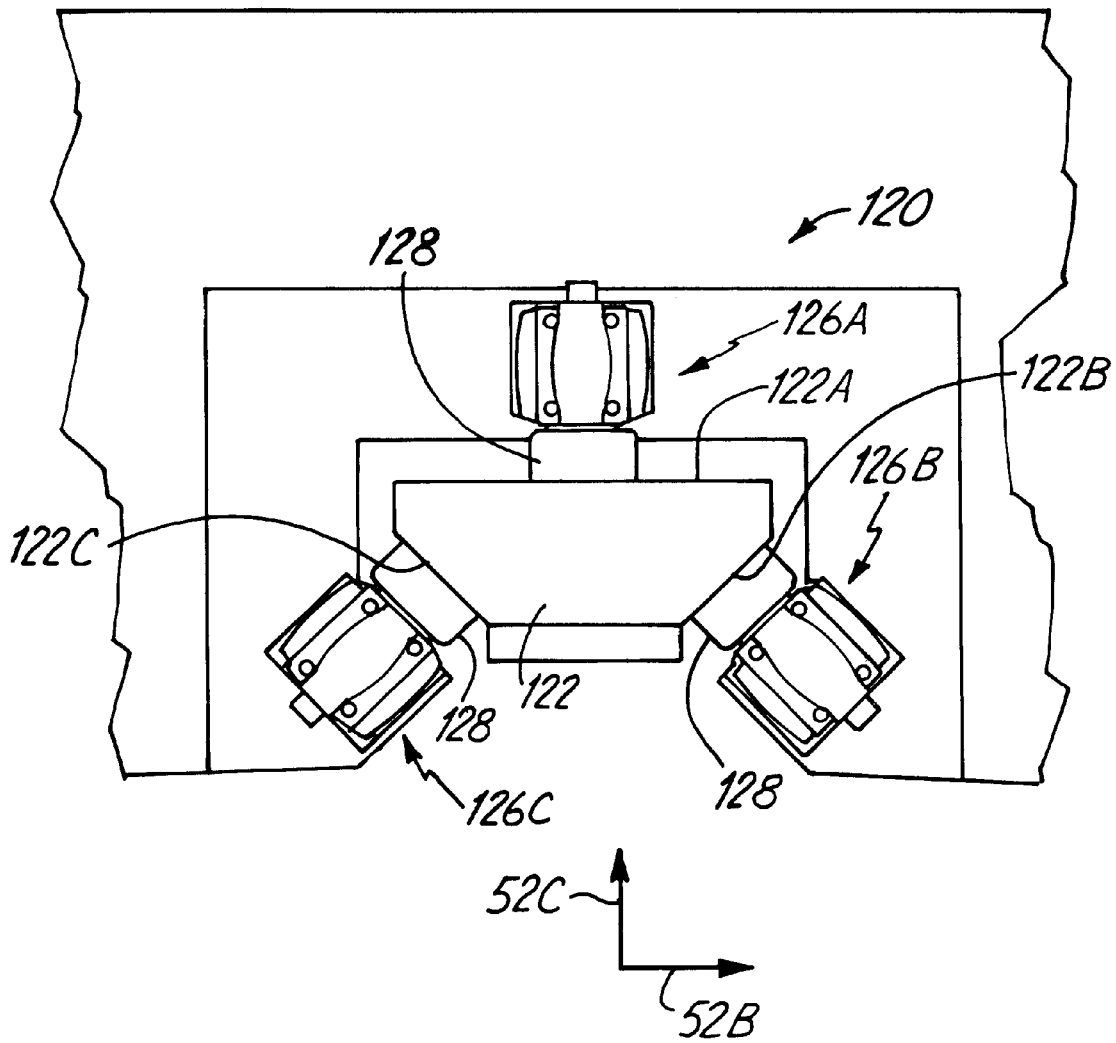
FIG. 7 is an enlarged front elevational view of a portion of a second embodiment of a load generating mechanism.

FIG. 7 illustrates a second embodiment of a load generating assembly 120 for displacing a moveable head 122. The load generating assembly 120 includes three spaced-apart actuator assemblies 126A, 126B and 126C to selectively displace the moveable head 122 along the axes 52B and 52C. In this embodiment, the moveable head 122 is triangularly shaped having planar surfaces 122A, 122B and 122C. Each of the actuator assemblies 126A–126C includes a planar hydrostatic bearings 128 that allows displacement of the moveable head 122 along the axes 52B and 52C while restraining rotational movement about the axis 52A. The planar hydrostatic bearings 82A–82B such as shown in FIG. 4 are provided and restrain all other degrees of freedom.

The material testing apparatus 10 of the present invention is particularly well suited for applying high frequency, mechanical loads in the presence of high static or slowly time-varying loads. By separating static or slowly time-varying loads (which are applied by the base assembly 14) from high frequency loads (which are applied from the load generating mechanisms 64 or 120), the material testing apparatus 10 has a wide operating range. In a preferred embodiment, the base assembly 14 allows controlled displacement from approximately 1–125 mm and can operate in a frequency range from approximately 0 to 20 Hz. In contrast, the maximum displacement of the head 62 or 122 by the load generating mechanism 64 or 120 is less than that of the base assembly 14, for example 0.005–5 mm, while the operating frequency range is greater than that available from the base assembly 14, for example, approximately 0.1 to 700 Hz. In one embodiment, the maximum displacement of components of the base assembly 14 is at least five times greater than the maximum displacement of the moveable head 62, while in a further embodiment, the maximum displacement of components of the base assembly 14 is at least ten times greater than the maximum displacement of the head 62. Likewise, in one embodiment, the maximum operating frequency of loads applied from the load generating mechanism 64 or 120 is at least ten times greater than the maximum operating frequency of loads applied from the base assembly 14. In yet a further embodiment, the operating frequency of loads applied from the load generating mechanism 64 or 120 is at least 15 times greater than the operating frequency of loads applied from the base assembly 14.

Although the present invention has been described with reference to preferred embodiments, workers skilled in the art will recognize that changes may be made in form and detail without departing from the spirit and scope of the invention.

What is claimed is:

1. A material testing apparatus for applying selected force and moment loads to a test specimen, the material testing apparatus comprising:
   a base assembly coupleable to the test specimen, the base assembly comprising:
      a first load generating mechanism adapted to apply a first load to the test specimen; and
      a support member; and
   a reaction structure for reacting the first load applied to the test specimen, the reaction structure comprising:
      a reaction support joined to the support member;
      a moveable head coupleable to the test specimen and moveable relative to the reaction support in at least two degrees of freedom; and
      a second load generating mechanism coupled to the moveable head and the reaction support, the second load generating mechanism adapted to apply selected loads to the test specimen in at least two degrees of freedom.

2. The material testing system of claim 1 wherein the first load generating mechanism is adapted to apply loads to the test specimen in at least two degrees of freedom.

3. The material testing system of claim 2 wherein the second load generating mechanism is adapted to apply loads to the test specimen in at least three degrees of freedom.

4. The material testing system of claim 1 wherein the support member includes spaced-apart supports coupled to the reaction support.

5. The material testing system of claim 4 wherein the spaced-apart supports are longitudinally adjustable.

6. The material testing system of claim 1 wherein the second load generating mechanism includes a plurality of spaced-apart actuators.

7. The material testing system of claim 6 wherein the second load generating mechanism includes three spaced-apart actuators.

8. The material testing system of claim 6 wherein the plurality of actuators are grouped in pairs wherein actuators of each pair engage opposed surfaces of the moveable head.

9. The material testing system of claim 6 wherein each actuator includes a planar hydrostatic bearing.

10. The material testing system of claim 9 wherein each actuator includes a rotational hydrostatic bearing.

11. The material testing system of claim 8 wherein the pairs of actuators comprise a first pair defining a first pair of parallel actuator lines, and a second pair defining a second pair of parallel actuator lines, wherein the first pair of actuator lines intersect orthogonally with the second pair of actuator lines.

12. The material testing system of claim 11 wherein the first pair of actuator lines are offset from each other, and wherein the second pair of actuator lines are offset from each other.

13. The material testing system of 6 wherein each actuator includes a piston moveable in a housing forming a first chamber and a second chamber, wherein the first chamber is capable of receiving fluid to apply the dynamic force and the second chamber is capable of receiving fluid to react the first load.

14. The material testing system of claim 13 wherein the first chamber is operably formed between the piston and a surface of the moveable head and the second chamber is operably formed between the piston and the reaction support.

15. The material testing system of claim 1 wherein the first load generating mechanism has a first maximum displacement and a first maximum operating frequency for applying the first load, and wherein the second load generating mechanism has a second maximum displacement and a second maximum operating frequency for applying the second load, wherein the first maximum displacement is greater than the second maximum displacement, and wherein the second maximum operating frequency is greater than the first maximum operating frequency.

16. The material testing system of claim 15 wherein the first maximum displacement is at least five times greater than the second maximum displacement.

17. The material testing system of claim 16 wherein the second maximum operating frequency is at least ten times greater than the first maximum operating frequency.

18. The material testing system of claim 17 wherein the first maximum displacement is at least ten times greater than the second maximum displacement.

19. The material testing system of claim 18 wherein the second maximum operating frequency is at least fifteen times greater than the first maximum operating frequency.

20. A material testing apparatus for applying selected force and moment loads to a test specimen, the material testing apparatus comprising:
   a base assembly coupleable to the test specimen, the base assembly comprising:
      a first load generating mechanism adapted to apply a first load to the test specimen; and
      a support member; and
   a reaction structure for reacting the first load applied to the test specimen, the reaction structure comprising:
      a reaction support joined to the support member;
      a moveable head coupleable to the test specimen and moveable relative to the reaction support in at least two degrees of freedom; and
      a plurality of spaced-apart actuators coupled to the moveable head and the reaction support, the plurality of spaced-apart actuators are oriented to apply selected loads to the test specimen in at least two degrees of freedom, wherein each actuator applies a linear force along a longitudinal axis of the actuator.

21. A material testing apparatus for applying selected force and moment loads to a test specimen, the material testing apparatus comprising:
   a base assembly coupleable to the test specimen, the base assembly comprising:
      a first load generating mechanism adapted to apply a first load to the test specimen; and
      a support member; and
   a reaction structure for reacting the first load applied to the test specimen, the reaction structure comprising:
      a reaction support joined to the support member;
      a moveable head coupleable to the test specimen and moveable relative to the reaction support; and
      means for applying selected loads to the test specimen through the movable head in at least two degrees of freedom.

22. The material testing system of claim 1 wherein the movable head of the reaction structure is movable relative to the reaction support in at least two degrees of freedom.

* * * * *